(12) United States Patent
Vuorenmaa et al.

(10) Patent No.: US 9,919,013 B2
(45) Date of Patent: Mar. 20, 2018

(54) USE OF TALL OIL FATTY ACID

(71) Applicant: Hankkija Oy, Hyvinkää (FI)

(72) Inventors: Juhani Vuorenmaa, Hyvinkää (FI); Hannele Kettunen, Tervakoski (FI)

(73) Assignee: Hankkija Oy, Hyvinkaa (FI)

( * ) Notice: Subject to any disclaimer, the term of this patent is extended or adjusted under 35 U.S.C. 154(b) by 5 days.

(21) Appl. No.: 14/891,060

(22) PCT Filed: May 9, 2014

(86) PCT No.: PCT/FI2014/050347
§ 371 (c)(1),
(2) Date: Nov. 13, 2015

(87) PCT Pub. No.: WO2014/184431
PCT Pub. Date: Nov. 20, 2014

(65) Prior Publication Data
US 2016/0081368 A1 Mar. 24, 2016

(30) Foreign Application Priority Data

May 14, 2013 (FI) ..................................... 20135506

(51) Int. Cl.
| A61K 36/15 | (2006.01) |
| A61K 36/13 | (2006.01) |
| A61K 31/19 | (2006.01) |
| A61K 31/20 | (2006.01) |
| A23K 20/158 | (2016.01) |
| A23K 50/10 | (2016.01) |
| A23L 33/115 | (2016.01) |

(52) U.S. Cl.
CPC ............ *A61K 36/15* (2013.01); *A23K 20/158* (2016.05); *A23K 50/10* (2016.05); *A23L 33/115* (2016.08); *A61K 31/19* (2013.01); *A61K 31/20* (2013.01); *A61K 36/13* (2013.01); *A23V 2002/00* (2013.01); *Y02P 60/56* (2015.11)

(58) Field of Classification Search
CPC .............................. A23L 33/115; A61K 20/158
See application file for complete search history.

(56) References Cited

U.S. PATENT DOCUMENTS

| 2,240,365 A | 4/1941 | Dreger |
| 2,308,431 A | 1/1943 | Brandt |
| 2,423,236 A | 7/1947 | Harwood et al. |
| 2,481,356 A | 9/1949 | Segessemann et al. |
| 2,530,810 A | 11/1950 | Christenson et al. |
| 2,611,706 A | 9/1952 | Bernhart et al. |
| 2,736,663 A | 2/1956 | Weber |
| 2,854,420 A | 9/1958 | Clark et al. |
| 2,866,739 A | 12/1958 | Ciesielski et al. |
| 2,894,939 A | 7/1959 | Hampton |
| 2,941,941 A | 6/1960 | Groll |
| 2,987,183 A | 6/1961 | Bishop |
| 3,001,962 A | 9/1961 | Carlston |
| 3,009,820 A | 11/1962 | Gould |
| 3,066,160 A | 11/1962 | Hampton |
| 3,175,916 A | 3/1965 | Costigliola et al. |
| 3,141,897 A | 7/1965 | Crecelius et al. |
| 3,194,728 A | 7/1965 | Stump, Jr. |
| 3,257,438 A | 6/1966 | Wicke et al. |
| 3,311,561 A | 3/1967 | Anderson et al. |
| 3,458,625 A | 7/1969 | Ensor et al. |
| 3,691,211 A | 4/1972 | Julian |
| 3,830,789 A | 8/1974 | Garrett et al. |
| 3,887,537 A | 6/1975 | Harada et al. |
| 3,926,936 A | 12/1975 | Lehtlnen |
| 4,000,271 A | 12/1976 | Kremer et al. |
| 4,076,700 A | 2/1978 | Harada et al. |
| 4,118,407 A | 10/1978 | Red et al. |
| 4,313,940 A | 2/1982 | Pasarela |
| 4,437,894 A | 3/1984 | Emerson |
| 4,443,437 A | 4/1984 | Prokosch et al. |
| 4,810,299 A | 3/1989 | Schilling et al. |
| 4,810,534 A | 3/1989 | Seaborne et al. |
| 5,428,072 A | 6/1995 | Cook et al. |
| 5,460,648 A | 10/1995 | Walloch et al. |
| 6,020,377 A | 2/2000 | O'Quinn et al. |
| 6,229,031 B1 | 5/2001 | Strohmaier et al. |
| 6,608,222 B2 | 8/2003 | Bonsignore et al. |
| 8,741,171 B2 | 6/2014 | Swift et al. |
| 9,358,218 B2 | 6/2016 | Vuorenmaa et al. |
| 9,422,507 B2 | 8/2016 | Hamunen |
| 2002/0147356 A1 | 10/2002 | Bonsignore et al. |
| 2002/0183298 A1 | 12/2002 | Schersl et al. |
| 2003/0144536 A1 | 7/2003 | Sonnier |

(Continued)

FOREIGN PATENT DOCUMENTS

| CA | 2 107 647 A1 | 4/1994 |
| CN | 101461443 A | 6/2009 |

(Continued)

OTHER PUBLICATIONS

European Search Report for European Patent Application No. 14797471.1 dated Dec. 6, 2016, 11 pgs.
European Search Report for European Patent Application No. 14797745.8 dated Dec. 5, 2016, 9 pgs.
European Search Report for European Patent Application No. 14797238.4 dated Dec. 7, 2016, 10 pgs.
Duncan, D.P., "Tall Oil Fatty Acids", *Naval Stores*, 346-349 (1989).
Gudmundur, B. et al., "Antibacterial, Antiviril and Antifungal Activities of Lipids" in "Lipids and Essential Oils as Antimicrobial Agents", *John Wiley & Sons*, 47-80 (2011)
Van Nevel, C.J. et al., "Effect of Fatty Acid Derivatives on Rumen Methane and Propionate In Vitro[1]", *Applied Microbiology*, 365-366 (1971).

(Continued)

*Primary Examiner* — Kyle A Purdy
(74) *Attorney, Agent, or Firm* — Merchant & Gould P.C.

(57) ABSTRACT

The present invention relates to use of a tall oil fatty acid in the modulation of microbial population of the animal digestive tract. The invention further relates to use of a feed supplement and a feed composition comprising tall oil fatty acid.

16 Claims, 2 Drawing Sheets

(56) References Cited

U.S. PATENT DOCUMENTS

Figure 1:
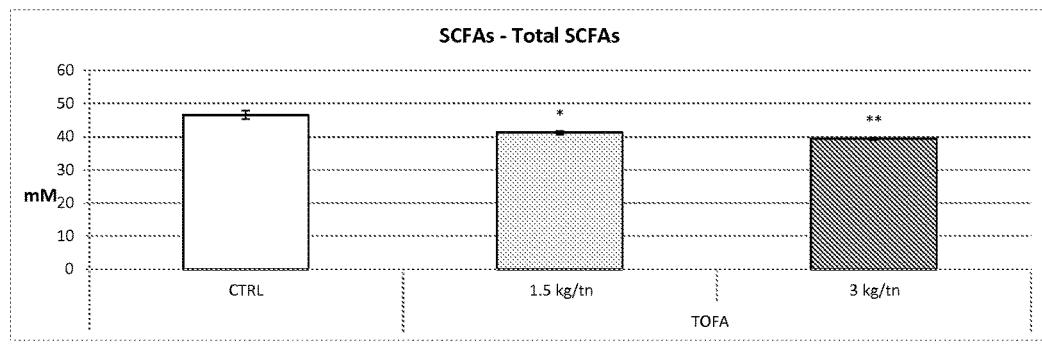

| | | | |
|---|---|---|---|
| 2005/0107582 | A1 | 5/2005 | Wong et al. |
| 2005/0203279 | A1 | 9/2005 | Rojas et al. |
| 2006/0021276 | A1 | 2/2006 | Sonnier |
| 2006/0286185 | A1 | 12/2006 | Prokosch |
| 2008/0262251 | A1 | 10/2008 | Sato et al. |
| 2009/0012164 | A1 | 1/2009 | Kelderman |
| 2009/0220638 | A1 | 9/2009 | Pablos Perez |
| 2009/0277972 | A1 | 11/2009 | Kennon et al. |
| 2009/0285931 | A1 | 11/2009 | Shelby et al. |
| 2009/0297687 | A1 | 12/2009 | Ramirez Marco et al. |
| 2011/0081442 | A1 | 4/2011 | Weill et al. |
| 2011/0200570 | A1 | 8/2011 | Mosbaugh et al. |
| 2011/0212217 | A1 | 9/2011 | Herranen et al. |
| 2011/0212218 | A1 | 9/2011 | Herranen et al. |
| 2012/0070516 | A1 | 3/2012 | Tranquil et al. |
| 2013/0041192 | A1 | 2/2013 | Saviainen et al. |
| 2015/0164966 | A1 | 6/2015 | Vuorenmaa et al. |
| 2015/0238454 | A1 | 8/2015 | Vuorenmaa et al. |
| 2016/0081952 | A1 | 3/2016 | Vuorenmaa et al. |
| 2016/0089407 | A1 | 3/2016 | Vuorenmaa et al. |
| 2016/0250171 | A1 | 9/2016 | Vuorenmaa et al. |
| 2016/0250269 | A1 | 9/2016 | Rintola et al. |

FOREIGN PATENT DOCUMENTS

| | | | | |
|---|---|---|---|---|
| DE | 101 06 078 | A1 | 9/2002 | |
| EP | 0 078 152 | A1 | 5/1983 | |
| EP | 0 146 738 | A2 | 7/1985 | |
| EP | 1 586 624 | A1 | 10/2005 | |
| EP | 1586624 | A1 * | 10/2005 | ........... C11B 13/005 |
| EP | 2 343 061 | A1 | 7/2011 | |
| FI | 41337 | B | 6/1969 | |
| FI | 20120287 | A | 4/2013 | |
| GB | 955316 | A | 4/1965 | |
| GB | 2 139 868 | A | 11/1984 | |
| GB | 2 271 282 | A | 4/1994 | |
| JP | S60-237008 | A | 11/1985 | |
| WO | WO 94/16690 | A1 | 8/1994 | |
| WO | WO 99/10148 | A1 | 3/1999 | |
| WO | WO 02/02106 | A1 | 1/2002 | |
| WO | WO 03/024681 | A1 | 3/2003 | |
| WO | WO 2006/040537 | A1 | 4/2006 | |
| WO | WO 2008/099051 | A2 | 8/2008 | |
| WO | WO 2008/154522 | A1 | 12/2008 | |
| WO | WO 2009/079680 | A1 | 7/2009 | |
| WO | WO 2009/106696 | A1 | 9/2009 | |
| WO | WO 2011/042613 | A2 | 4/2011 | |
| WO | WO 2011/055018 | A2 | 5/2011 | |
| WO | WO 2011/080399 | A1 | 7/2011 | |
| WO | WO 2011/099000 | A2 | 8/2011 | |
| WO | WO 2012/037297 | A1 | 3/2012 | |
| WO | WO 2013/060936 | A1 | 5/2013 | |
| WO | WO 2013/118099 | A1 | 8/2013 | |
| WO | WO 2013/171370 | A1 | 11/2013 | |
| WO | WO 2014/184430 | A1 | 11/2014 | |

OTHER PUBLICATIONS

"Explanatory Notes to the Harmonized Commodity Description and Coding System", The Department of Duty Collection of the 25 General Administration of Customs, China Commerce and TradePress, published on Jan. 31, 2007, see p. 478: "Tall Oil, Whether or Not Refined". English translation of relevant parts.

Huwig, A. et al., "Mycotoxin detoxication of animal feed by different adsorbents", *Toxicology Letters*, 122: 179-188 (2001).

Magee, T. et al., "Composition of American Distilled Tall Oils", *JAOCS*, 69(4): 321-324 (1992).

Shetty, P. et al., "*Saccharomyces cerevisiae* and lactic acid bacteria as potential mycotoxin decontaminating agents", *Trends in Food Science & Technology*, 17: 48-55 (2006).

Antila, M. et al., "The fatty acids of tall oil and their ethyl and glyceryl esters as animal fodder ingredients, the chemical and physical properties of the fatty acid fraction and esters prepared from this fraction", *Journal ACTA Agdcultureae Scandinavia*, 12: 95-105, 1962, Abstract.

Bannink, A. et al., "A model of enteric fermentation in dairy cows to estimate methane emission for the Dutch National Inventory Report using the IPCC Tier 3 approach", 166-167: 603-618, 2011.

Beauchemic, K.A., et al., "Nutritional management for enteric methane abatement: a review", *Australian Journal of Experimental Agriculture*, 48: 21-27, 2008.

de Graaf et al., "Consumption of tall oil-derived phytosterols in a chocolate matrix significantly decreases plasma total and low-density lipoprotein-cholesterol levels", *British Journal of Nutrition*, 88: 479-488, 2002.

Grainger, C. et al., "Can enteric methane emissions from ruminants be lowered without lowering their production?", *Animal Feed Science and Technology*, 166-167: 308-320, 2011.

Machmüller, A., "Medium-chain fatty acids and their potential to reduce methanogenesis in domestic ruminants", *Agriculture, Ecosystems and Environment*, 112: 107-114, 2006.

Machmüller, A. et al., "Potential of various fatty feeds to reduce methane release from rumen fermentation in vitro (Rushee)", *Animal Feed Science Technology*, 71: 117-130, 1998.

McGuire, J. et al., "Gas Chromatographic Analysis of Tall Oil Fractionation Products After Methylation with N,N-Dimethylformamide Dimethylacetal", *Journal of Chromatographic Science*, 36: 104-108, 1998.

Norlin, L. "Tall Oil", *Ullmann's Encyclopedia of Industrial Chemistry*, published online: Jun. 15, 2000.

O'Quinn, P.R. et al., "Effects of modified tall oil and creatine monohydrate on growth performance, carcass characteristics, and meat quality of growing-finishing pigs", *Journal of Animal Science*, 78(9): 2376-2382, 2000.

O'Quinn, P.R. et al., "Effects of modified tall oil versus a commercial source of conjugated linoleic acid and increasing levels of modified tall oil on growth performance and carcass characteristics of growing-finishing pigs", *Journal of Animal Science*, 78(9): 2359-2368, 2000.

O'Quinn, P.R. et al., "Effects of modified tall oil versus conjugated linoleic acid on finishing pig growth performance and carcass characteristics", *KSU Swine Day*, 157-161, 1998.

Patra, A.K., "Effects of Essential Oils on Rumen Fermentation, Microbial Ecology and Ruminant Production", *Asian Journal of Animal and Veterinary Advances*, 6(5): 416-428, 2011.

Polan, C.E. et al., "Biohydrogenation of Unsaturated Fatty Acids by Rumen Bacteria", *Journal of Bacteriology*, 88(4): 1056-1064, 1964.

Savluchinske-Feio, S. et al., "Antimicrobial activity of resin acid derivatives", *Applied microbiology and Biotechnology*, 72(3): 430-436, 2006.

Smith, E., et at, "Isopimaric Acid from Pinus nigra shows Activity against Multi-drug-resistant and EMRSA Strains for *Staphylococcus aureus*", *Phytotherapy Research*, 19(6): 538-542, 2005.

Snell, F. et al., "Comparative Value of Fatty Acids and Resin Acids of Tall Oil in Soaps", *The Journal of the American Oil Chemist's Society*, 27(8): 289-295; 1950.

Zhou, X. et al., "The Effect of Saturated Fatty Acids on Methanogenesis and Cell Viability of *Methanobrevibacter ruminantium*", *Archaea*, 2013: 1-9, 2013.

International Search Report for International Patent Application No. PCT/2014/050347 dated Oct. 23, 2014.

Finnish Search Report for Finnish Patent Application No. 20135506 dated Dec. 20, 2013.

Product Data Sheet SYLFAT® 2LTC tall oil fatty acid [online], Arizona Chemical, [last modified Jul. 20, 2009], retrieved Dec. 17, 2013, URL: hup://www.arizonachemical.com/Global/PDS/EU_product_data_sheets/SYLFAT%C2%AE%202LTC.pdf.

* cited by examiner

USE OF TALL OIL FATTY ACID

This application is a National Stage Application of PCT/FI2014/050347, filed 9 May 2014, which claims benefit of Serial No. 20135506, filed 14 May 2013 in Finland and which applications are incorporated herein by reference. To the extent appropriate, a claim of priority is made to each of the above disclosed applications.

The invention relates to use of a tall oil fatty acid and feed supplement and feed composition comprising said tall oil fatty acid.

BACKGROUND OF THE INVENTION

Imbalances in microbial populations and growth of harmful bacteria in the digestive tract of animals can cause significant losses in animal growth and production. These imbalances manifest themselves as intestinal disorders such as diarrhea. While microbial infections of animals have been prevented by the use of e.g. antibiotics and other agents that prevent the growth of microorganisms, stricter regulations on their use are expected. Generally, there is an increasing demand for ingredients for use in animal feeding that can modulate the microbial population in the animal digestive tract but which are readily available, well tolerated and environmentally friendly.

Fractional distillation of crude tall oil, obtained as a by-product of the Kraft process of wood pulp manufacture, produces distilled tall oil (DTO) which typically comprises over 10% resin acids and less than 90% fatty acids. Further refinement of distilled tall oil produces tall oil fatty acid (TOFA), which is available in a variety of compositions differing in the fatty acids and resin acids content. Because TOFA is an inexpensive source of fatty acids, it has previously been used in animal nutrition as an energy source. For instance, GB 955316 discloses the use of alkali metal salts of tall oil fatty acids to improve weight gain and nitrogen retention in ruminant animals.

PURPOSE OF THE INVENTION

The purpose of the invention is to provide a new type of tall oil fatty acid/feed supplement for use in the modulation of microbial population of the animal digestive tract.

The present inventors have surprisingly found that TOFA modulates microbial population of the animal digestive tract.

SUMMARY

A method of modulation of a microbial population of an animal digestive tract is provided. The method includes: (a) feeding tall oil fatty acid to the animal, wherein the tall oil fatty acid comprises 1-10% (w/w) resin acids, wherein the tall oil fatty acid is produced by distillation of crude tall oil to form distilled tall oil, and by further refinement of the distilled tall oil to form the tall oil fatty acid; and (b) modulating the microbial population in the animal digestive tract.

A method of modulation of a microbial population of an animal digestive tract is provided. The method includes: (a) feeding a feed supplement to the animal wherein the feed supplement comprises tall oil fatty acid, wherein the tall oil fatty acid comprises 1-10% (w/w) resin acids, wherein the tall oil fatty acid is produced by distillation of crude tall oil to form distilled tall oil, and by further refinement of the distilled tall oil to form the tall oil fatty acid; and (b) modulating the microbial population in the animal digestive tract.

A method of modulation of a microbial population of an animal digestive tract is provided. The method includes: (a) feeding a feed composition to the animal wherein the feed composition comprises a feed supplement comprising tall oil fatty acid, wherein the tall oil fatty acid comprises 1-10% (w/w) resin acids, wherein the tall oil fatty acid is produced by distillation of crude tall oil to form distilled tall oil, and by further refinement of the distilled tall oil to form the tall oil fatty acid; and (b) modulating the microbial population in the animal digestive tract.

DETAILED DESCRIPTION OF THE INVENTION

FIG. 1. Effect of TOFA on the total SCFA production in the ileal simulation.

Figure 2:
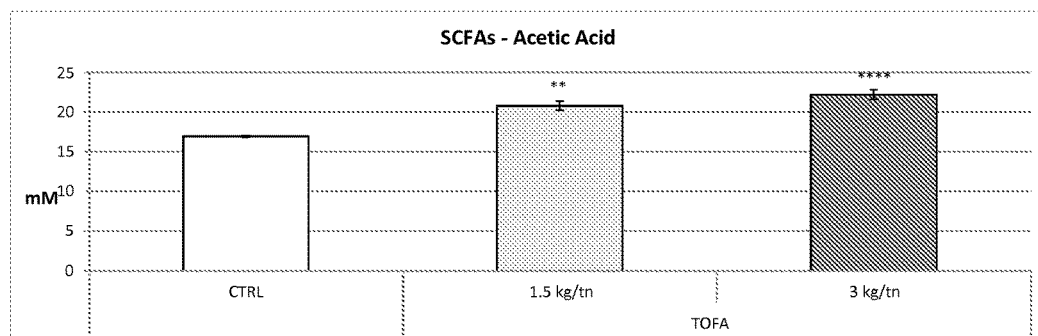

FIG. 2. Effect of TOFA on the acetic acid production in the ileal simulation.

Figure 3:
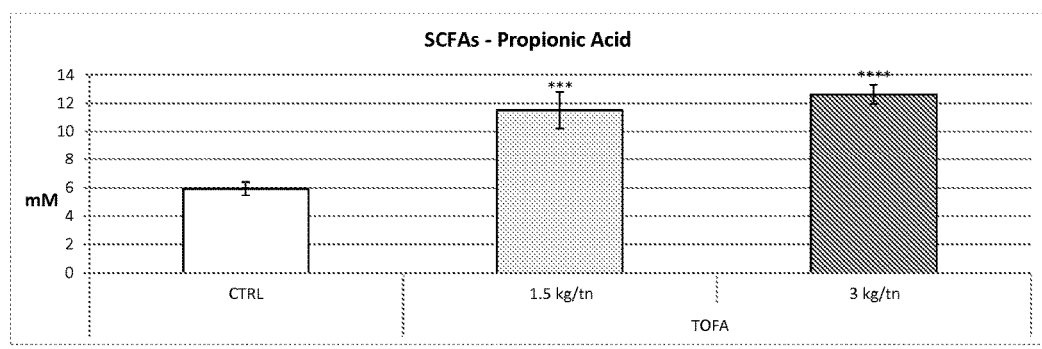

FIG. 3. Effect of TOFA on the propionic acid production in the ileal simulation.

Figure 4:
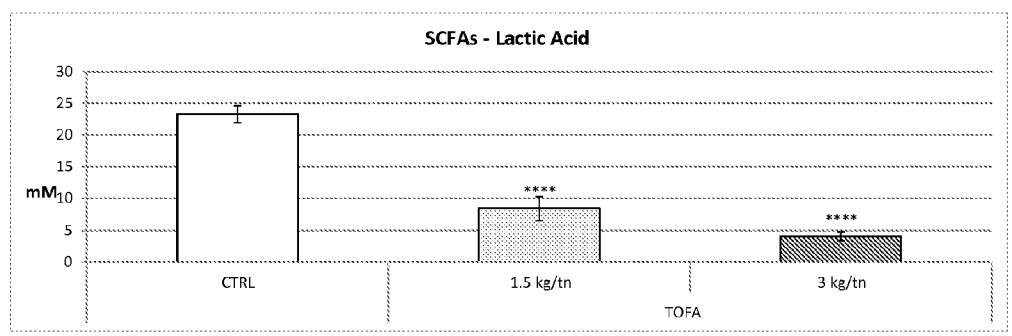

FIG. 4. Effect of TOFA on the lactic acid production in the ileal simulation.

The present invention is based on the realization that tall oil fatty acid can be used in the modulation of microbial population of the animal digestive tract.

The modulation of microbial population of the animal digestive tract is carried from homofermentatine towards heterofermentative metabolical route and in one embodiment of the present invention it improves the feed utilization (improved nutritional value). In another embodiment of the present invention, the modulation of microbial population of the animal digestive tract improves the feed conversion ratio.

The term "tall oil fatty acid" or "TOFA" should be understood as referring to a composition obtained by distillation of crude tall oil and further refinement of distilled tall oil. TOFA typically comprises 90-98% (w/w) fatty acids. Further, TOFA may comprise 1-10% (w/w) resin acids.

In one embodiment of the present invention, the tall oil fatty acid comprises 1-10% (w/w) of resin acids.

In one embodiment of the present invention, TOFA comprises 2-9% (w/w) resin acids.

In one embodiment of the present invention, TOFA comprises 5-9% (w/w) resin acids. In this context, the term "resin acids" should be understood as referring to a complex mixture of various acidic compounds comprised by tall oil which share the same basic skeleton including a three-fused ring. The exact composition of the resin acids present in TOFA varies e.g. according to the species of the trees the TOFA is obtained from and the processing conditions under which it is manufactured. Resin acids typically include compounds such as abietic acid, dehydroabietic acid, levopimaric acid, neoabietic acid, pimaric acid and isopimaric acid, only to mention a few.

In one embodiment of the present invention, TOFA comprises 90-98% (w/w) of fatty acids.

The tall oil fatty acid (TOFA) is produced by refinement from distilled tall oil. Distilled tall oil (DTO) is produced by fractional distillation from crude tall oil, obtained as a by-product of the Kraft process of wood pulp manufacture.

In one embodiment of the present invention, the TOFA is dried. The TOFA can be dried by spray drying, drum drying or by any other known suitable drying method.

The present invention also relates to use of a feed supplement comprising the tall oil fatty acid in the modulation of microbial population of the animal digestive tract.

The feed supplement of the present invention is effective in the modulation of microbial population of the animal digestive tract.

In one embodiment of the present invention, the feed supplement comprises a tall oil fatty acid which comprises 1-10% (w/w) resin acids.

In one embodiment of the present invention, the feed supplement comprises a tall oil fatty acid which comprises 2-9% (w/w) resin acids. In one embodiment of the present invention, the feed supplement comprises a tall oil fatty acid which comprises 5-9% (w/w) resin acids.

In this context, the term "feed supplement" should be understood as referring to a composition that may be added to a feed or used as such in the feeding of animals. The feed supplement may comprise different active ingredients. The feed supplement may be added in the feed in a concentration of 0.0001-5 kg//ton of dry weight, preferably 0.005-1 kg/ton of the dry weight of the total amount of the feed. The TOFA or the feed supplement comprising the TOFA according to the invention may be added to the feed or feed supplement as such, or it may in general be further processed as desired.

Further, the TOFA or the feed supplement comprising the TOFA according to the invention may be added to the feed or feed supplement, or it may be administered to an animal separately (i.e. not as a part of any feed composition).

In this context, the term "feed composition" or "feed" should be understood as referring to the total feed composition of an animal diet or to a part thereof, including e.g. supplemental feed, premixes and other feed compositions. The feed may comprise different active ingredients.

In one embodiment of the present invention, the feed supplement comprises TOFA which is absorbed into a carrier material suitable for the feed composition such as sugarbeet pulp.

In one embodiment of the present invention, the feed supplement comprises TOFA which is dried.

The present invention also relates to use of a feed composition comprising the feed supplement comprising the tall oil fatty acid in the modulation of microbial population of the animal digestive tract.

In one embodiment of the present invention, the feed composition comprises the feed supplement in an amount of 0.00001-0.5% (w/w), of the dry weight of the total amount of the feed.

In one embodiment of the present invention, the feed composition comprises the feed supplement in an amount of 0.0005-0.1% (w/w) of the dry weight of the total amount of the feed.

In one embodiment of the present invention, the method of producing a tall oil fatty acid or feed supplement further comprises a step of drying. The dying can be carried out by spray drying, drum drying or by any other known drying method.

The invention also relates to a method of modulating microbial population of the animal digestive tract, comprising the step of administering to an animal the tall oil fatty acid according to the invention.

In this context, the term "harmful bacteria" should be understood as referring to any bacteria that is capable of affecting the digestive tract or health of an animal in an adverse manner, including competition for nutrients with the host animal. In this context, the term "microbial population" should be understood as referring to the microorganisms that inhabit the digestive tract, including the Bacteria and Archaea domains and microscopic members of the Eukaryote domain and also intestinal parasites. The microbial population will vary for different animal species depending on e.g. the health of an animal and on environmental factors.

In this context, the term "animal" should be understood as referring to all kinds of different animals, such as monogastric animals, ruminants, fur animals, pets and aquaculture. Non-limiting examples of different animals, including offspring, are cows, beef cattle, pigs, poultry, sheep, goats, horses, foxes, dogs, cats and fish.

In one embodiment of the present invention, the TOFA is administered to an animal in an effective amount.

The present invention has a number of advantages. TOFA is a readily available, natural, low-cost and environmentally friendly material. Further, it is non-toxic and well tolerated. The invention is effective in modulating the composition of the microbiota in the animal digestive tract to a direction that is beneficial for animal performance. Subsequently, other benefits of the invention are e.g. improved animal productivity, improved feed conversion ratio, higher product quality, uniformity, nutritional value and food and product safety and lower costs per production unit. The invention also allows the production of feed compositions and supplements at low cost.

The embodiments of the invention described hereinbefore may be used in any combination with each other. Several of the embodiments may be combined together to form a further embodiment of the invention. A product, a method or a use, to which the invention is related, may comprise at least one of the embodiments of the invention described hereinbefore.

EXAMPLES

In the following, the present invention will be described in more detail.

Example 1

This experiment was conducted to study the effect of TOFA with 5% resin acids with or without Sugar Beet Pulp (SBP) carrier on the microbial population and fermentation of broiler chick ileum in vitro.

Experiment

Ileal contents of 40-days old broiler chicks were used for the simulation media and as inoculants in the simulation models. The trial treatments were prepared from a batch of TOFA.

Preparations of TOFA with 5% resin acids were produced:
1. TOFA with 20% dry matter content An aliquot of the TOFA was heated to 90° C., mixed with finely ground SBP powder, and dried to contain 375 g dry TOFA/kg.

2. Digested TOFA

Gastrointestinal digestion of the TOFA: Part of the liquid TOFA and the carrier-absorbed TOFA was digested by a pepsin-HCl-treatment (pH 2.25) followed by a pancreatin bile-acid-NaOH treatment (pH 6.2) in a dilution series. The digestion was made to evaluate whether the products would resist the conditions of the upper gastrointestinal tract before they enter the distal intestine with higher microbial activity.

The simulation was conducted in a total of 160 2-ml plastic microcentrifuge vials, in 1.5 ml volume, with 10 hours simulation time. Samples were tested at four concentrations of the dry matter of TOFA: 0%, 0.005%, 0.01%, 0.01% and 1%.

All the simulation samples were analysed for short chain fatty acids and the total number of microbes. In addition, selected samples were analysed for a number of microbial species or groups by quantitative real-time PCR (qPCR). Ileal simulation samples were analysed for *lactobacilli*, *enterococci* and *streptococci*.

Results

The results show that in the ileal simulation model, TOFA at 1 kg/ton level increased the concentrations of acetic and propionic acids and decreased the concentration of lactic acid. This suggests modulation of microbial metabolism from homofermentative towards heterofermentative metabolical route, which can be seen as a very positive change improving the feed conversion ratio. TOFA amendment at 0.1 kg/ton negatively affected the population numbers of *lactobacilli*, *enterococci* and *streptococci*, all of which are lactate producers. The total bacterial numbers in the ileum were not affected by the TOFA, which may indicate that other bacterial populations were increased as a response to the TOFA amendment. Pre-digestion of the TOFA affected many of the studied parameters, while the sugar beet pulp carrier had little effect on the fermentation.

Example 2

This experiment was conducted to study the effect of TOFA with 5% resin acids on nutritional value of feed and feed conversion ratio.

Experiment 240 newly-hatched, male Ross 508 broiler chicks were allocated into 40 open pens, six birds per pen and eight replicate pens per feeding treatment.

TOFA with 5% resin acid content was absorbed into ground sugar beet pulp (SBP) carrier and added to the feeds. The feed was wheat-soy-based starter formula. The dietary treatments:

| 1. | Control, no TOFA | |
|---|---|---|
| 2. | Control + TOFA 0.1% | (1 kg/ton) |
| 3. | Control + TOFA 0.05% | (500 g/ton) |
| 4. | Control + TOFA 0.01% | (100 g/ton) |

Chicks were weighed on days 1, 11, 14, and 17. Feed consumption was measured and feed conversion ratio (FCR) was calculated for the same periods. Daily mortality was recorded.

After day 17, 105 ileal and 105 cecal digesta samples were analysed for short chain fatty acids (SCFAs) with gas chromatography and a number of microbial species or groups by qPCR.

Results

The results show that the dietary TOFA with 5% resin acids, fed at the level of 0.1-1 kg/ton, dose-dependently increased the body weight of broiler chicks on days 8, 11, and 14. TOFA at 0.1-1 kg/ton favourably and dose-dependently modulated the small intestinal microbial fermentation from homofermentative to heterofermentative direction. Ileal and cecal numbers of *Cl. perfringens* were not significantly affected by dietary TOFA amendment. TOFA at 0.5 kg/tn decreased the frequency of samples with more than $1*10^9$ cells of *enterococci* or *streptococci*, or more than $1*10^{12}$ cells of *lactobacilli*. TOFA at 1 kg/ton decreased the frequency of samples with high counts of *streptococci* or *lactobacilli*.

The results show that the TOFA modulates the microbial population of the digestive tract of broiler chicks or other species of poultry if given in the feed and improve the feed conversion ratio.

Example 3

This experiment was conducted to study the effect of TOFA with 9% resin acids on the microbial population and fermentation of swine small-intestine in vitro Experiment The trial treatments were prepared from TOFA oil with 9% resin acid content. To mimic the conditions prevailing in stomach and duodenum of live piglet, the tested product was initially treated by pepsin-HCl (pH 3-4) for 1 hour and by bile acid+pancreatin+NaOH (pH 6.8-7.2) for 3 hours) at 37° C. prior to introducing them in the simulation vessels. Samples were tested at two concentrations of the dry matter of TOFA: 0, 1.5 and 3.0 kg/tn i.e. 0%, 0.15% and 0.3%).

For the authentic anaerobic growth medium of the small-intestine simulation, distal ileal digesta of 5 piglets (25-30 kg) was recovered and pooled. The digesta was subsequently centrifuged to remove the solid particles and combined with buffer solution (pH 6.5). The final growth medium prepared was maintained anaerobic and treated with TOFA at two doses.

Inoculum from fresh pooled ileal digesta of two piglets was introduced into simulation vessels in an anaerobic glove box. After inoculation, the vessels were sealed with thick butyl rubber stoppers, transferred to 37° C. and continuously mixed in a gyratory shaker at 100 r.p.m. The simulations had 5 replicate vessels for each TOFA concentrations, and the inoculation was performed in a random order to avoid any potential systematic shifts. Incubation was continued for 10 hours prior to sampling of the vessels for microbial metabolic analyses.

The simulation was conducted in a total of 25 20-ml glass vials, in 10 ml volume, with 10 hours simulation time.

All the simulation samples were analysed for total short-chain fatty acids as well as acetic, propionic and lactic acids.

Results

The results are illustrated in FIGS. 1-4.

In the ileal simulation model, inhibition of the total Short-chain fatty acid (SCFA) formation with TOFA treatments was observed (FIG. 1). The magnitude of inhibition was −11 to −14% from the control.

TOFA increased the concentrations of acetic (+23 to +31%) and propionic (+94% to +113%) acids and decreased the concentration of lactic acid (−64% to −82%) in a dose-dependent manner from the control treatment (FIGS. 2 to 4). This suggests modulation of microbial metabolism from homofermentative towards heterofermentative metabolical route, which can be seen as a very positive change.

It is obvious to a person skilled in the art that, with the advancement of technology, the basic idea of the invention may be implemented in various ways. The invention and its embodiments are thus not limited to the examples described above; instead they may vary within the scope of the claims.

The invention claimed is:

1. A method of modulation of a microbial population of an animal digestive tract comprising:
   (a) feeding tall oil fatty acid to the animal, wherein the tall oil fatty acid comprises 1-10% (w/w) resin acids, wherein the tall oil fatty acid is produced by distillation of crude tall oil to form distilled tall oil, and by further refinement of the distilled tall oil to form the tall oil fatty acid; and (b) modulating the microbial population in the animal digestive tract.

2. The method of modulation according to claim 1, wherein the tall oil fatty acid comprises 2-9% (w/w) resin acids.

3. The method of modulation according to claim 1, wherein the tall oil fatty acid comprises 5-9% (w/w) resin acids.

4. The method of modulation according to claim 1, wherein the tall oil fatty acid comprises 90-98% (w/w) fatty acids.

5. A method of modulation of a microbial population of an animal digestive tract comprising:
(a) feeding a feed supplement to the animal wherein the feed supplement comprises tall oil fatty acid, wherein the tall oil fatty acid comprises 1-10% (w/w) resin acids, wherein the tall oil fatty acid is produced by distillation of crude tall oil to form distilled tall oil, and by further refinement of the distilled tall oil to form the tall oil fatty acid; and
(b) modulating the microbial population in the animal digestive tract.

6. The method of modulation according to claim 5, wherein the tall oil fatty acid comprises 2-9% (w/w) resin acids.

7. The method of modulation according claim 5, wherein the tall oil fatty acid is absorbed into a carrier material.

8. A method of modulation of a microbial population of an animal digestive tract comprising:
(a) feeding a feed composition to the animal wherein the feed composition comprises a feed supplement comprising tall oil fatty acid, wherein the tall oil fatty acid comprises 1-10% (w/w) resin acids, wherein the tall oil fatty acid is produced by distillation of crude tall oil to form distilled tall oil, and by further refinement of the distilled tall oil to form the tall oil fatty acid; and
(b) modulating the microbial population in the animal digestive tract.

9. The method of modulation according to claim 8, wherein the feed composition comprises the feed supplement in an amount of 0.00001-0.5% (w/w) of dry weight of total amount of the feed.

10. The method of modulation according to claim 8 wherein the feed composition comprises the feed supplement in an amount of 0.0005-0.1% (w/w) of dry weight of total amount of the feed.

11. The method of modulation according to claim 8, wherein the tall oil fatty acid comprises 2-9% (w/w) resin acids.

12. The method of modulation according to claim 8, wherein the tall oil fatty acid comprises 5-9% (w/w) resin acids.

13. The method of modulation according to claim 8, wherein the modulation comprises a modulation of microbial metabolism from homofermentative toward heterofermentative metabolic route.

14. The method of modulation according to claim 1, wherein the modulation comprises a modulation of microbial metabolism from homofermentative toward heterofermentative metabolic route.

15. The method of modulation according to claim 5, wherein the tall oil fatty acid comprises 5-9% (w/w) resin acids.

16. The method of modulation according to claim 5, wherein the modulation comprises a modulation of microbial metabolism from homofermentative toward heterofermentative metabolic route.

* * * * *